United States Patent
Granados et al.

(10) Patent No.: US 7,179,648 B2
(45) Date of Patent: Feb. 20, 2007

(54) CLONAL CELL LINES DERIVED FROM BTI-TN-5B1-4

(75) Inventors: Robert R. Granados, Ithaca, NY (US); Guoxun Li, Qingdao (CN)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 0 days.

(21) Appl. No.: 10/532,288

(22) PCT Filed: Nov. 14, 2003

(86) PCT No.: PCT/US03/36395

§ 371 (c)(1), (2), (4) Date: Apr. 21, 2005

(87) PCT Pub. No.: WO2004/046318

PCT Pub. Date: Jun. 3, 2004

(65) Prior Publication Data

US 2006/0019384 A1  Jan. 26, 2006

Related U.S. Application Data

(60) Provisional application No. 60/426,535, filed on Nov. 15, 2002.

(51) Int. Cl.
- *C12N 5/00* (2006.01)
- *C12N 5/02* (2006.01)
- *C12N 5/06* (2006.01)
- *C12N 5/10* (2006.01)

(52) U.S. Cl. .................................. 435/348; 435/325

(58) Field of Classification Search ................ None
See application file for complete search history.

(56) References Cited

U.S. PATENT DOCUMENTS

| | | | |
|---|---|---|---|
| 5,298,418 A | 3/1994 | Granados | 435/348 |
| 5,300,435 A | 4/1994 | Granados | 435/348 |
| 5,686,305 A | 11/1997 | Wang et al. | 435/348 |
| 6,379,958 B1 | 4/2002 | Vaughn et al. | 435/348 |
| 6,403,375 B1 | 6/2002 | Granados | 435/348 |

OTHER PUBLICATIONS

Grace, T.D.C., Establishment of four strains of cells from insect tissue grown in vitro, Nature, vol. 195, p. 788-789, 1962.

Weiss, S.A. and J.L. Vaughn, Cell culture methods for large-scale propagation of baculovirus, in "The Biology of Baculoviruses," vol. II, "Practical Application for Insect Control" (Granados and Federici, Eds., CRC Press, Boca Raton, FL), pp. 63-87 (1986).

Granados et al., Production on viral agents in invertebrate cell cultures, in "Biotechnology in Invertebrate Pathology and Cell Culture" (Maramorosch, K., Ed., Academic Press, San Diego/NY), pp. 167-181, (1987).

Vaughn, in Invertebrate Tissue Culture, Research Applications Academic Press, NY/London, 1976, pp. 295-303.

Luckow, V.A. and M.D. Summers, High level expression of non-fused foreign genes with *Autographa californica* nuclear polyhedrosis virus expression vectors, Virology, 170:311-39 (1988).

Granados et al., Replication of the *Trichoplusia ni* Granulosis and Nuclear Polyhedrosis Viruses in cell cultures, Virology 152: 472-476 (1986).

Rochford et al., "Establishment of a cell line from embryos of that cabbage looper, *Trichoplusia ni* (Hubner)" In Vitro vol. 20, No. 11. p. 823-825, 1984.

Granados et al., "A New Insect Cell Line from *Trichoplusia ni* (BTI-Tn-5B1-4) Susceptible to *Trichoplusia ni* Single Enveloped Nuclear Polyhedrosis Virus." Journal of Invertebrate Pathology 64, 1994, p. 260-266.

O'Reilly et al., 1992, Baculovirus expression vectors, A laboratory manual, W.H. Freeman and Company, NY). 1992.

Shuler et al., 1995, Baculovirus Expression Systems and Biopesticides, Wiley-Liss Inc., NY. 1995, p. 121-130.

Donaldson and Shuler, "Effects of Long-Term Passagaing of BTI-Tn5B1-4 Insect Cells on Growth and Recombinant Protein Production" 1998, Biotechnol. Prog., 14, 543-547.

Hayflick, "Subculturing human diploid fibroblast cultures", from "Tissue Culture" Kruse and Patterson, Eds., New York: Academic Press 1973, pp. 220-223.

Corsaro and Fraser "Characterization of clonal populations of the Heliothis zea cell line IPLB-HZ 1075", In Vitro Cell. Dev. Bio. 23(12):855-862, 1987.

Harris and Hopkinson "Handbook of Enzyme Electrophoresis in Human Genetics," Amsterdam: North Holland Publishing Co. (1977), p. 68-69.

*Primary Examiner*—David M. Naff
*Assistant Examiner*—Deborah K. Ware
(74) *Attorney, Agent, or Firm*—Brown & Michaels, PC

(57) ABSTRACT

Improved insect cell lines, two of which are designated H5CL-B and H5CL-F (both of which are derived from the parental cell line BTI-TN-5B1-4, ATCC CRL 10859), possess the properties of increased production of baculovirus particles, increased expression of foreign proteins using a baculovirus expression system, and increased resistance to cell culture stress, relative to the parental cell line.

2 Claims, 3 Drawing Sheets

US 7,179,648 B2

CLONAL CELL LINES DERIVED FROM BTI-TN-5B1-4

REFERENCE TO RELATED APPLICATIONS

This application claims an invention which was disclosed in Provisional Application No. 60/426,535, filed Nov. 15, 2002, entitled "IMPROVED CLONAL CELL LINES DERIVED FROM BTI-TN-5B1-4". The benefit under 35 USC § 119(e) of the United States provisional application is hereby claimed, and the aforementioned application is hereby incorporated herein by reference in its entirety.

BACKGROUND OF THE INVENTION

1. Field of the Invention

The invention pertains to the field of cell lines derived from insects. More particularly, the invention pertains to improved cell lines that are susceptible to baculovirus infection and are useful for replicating such viruses, and are useful for gene expression using a baculovirus expression system.

2. Description of Related Art

Insect cell culture has been used broadly in insect virology research since the first insect cell line was established in 1962 (Grace, T. D. C., Establishment of four strains of cells from insect tissue grown in vitro, Nature, 195:788–789). The general use of tissue cell lines for the culture or replication of pathogenic microorganisms is well established, and production of viral insecticides in cell culture has many advantages over their cultivation in vivo ((Weiss, S. A. and J. L. Vaughn, Cell culture methods for large-scale propagation of baculovirus, in "The Biology of Baculoviruses," vol. II "Practical Application for Insect Control" (Granados and Federici, Eds., CRC Press, Boca Raton, Fla.), pp. 63–87 (1986)) and (Granados et al., Production on viral agents in invertebrate cell cultures, in "Biotechnology in Invertebrate Pathology and Cell Culture" (Maramorosch, K., Ed., Academic Press, San Diego/NY), pp. 167–181, (1987)). However, specific microorganisms cannot be cultured in all cell lines, even in all cell lines from the same order. Vaughn, in Invertebrate Tissue Culture, Research Applications (Academic Press, NY/London, 1976, pp. 295–303) discusses the development of insect cell lines and notes that, for example, cell lines from *Heliothis zea* are not capable of complete replication of the nuclear polyhedrosis virus obtained from *Heliothis zea* itself.

In recent years, baculovirus expression vectors have been widely used as vectors for foreign gene expression in insect cells (Luckow, V. A. and M. D. Summers, High level expression of non-fused foreign genes with *Autographa californica* nuclear polyhedrosis virus expression vectors, Virology, 170:311–39 (1988)). Therefore, insect cell culture has become more important as a potentially attractive system for producing viral insecticides and expressing foreign gene products of interest in the areas of biology, medicine, and agriculture.

Cell lines from *Trichoplusia ni* eggs have been established and infected ((Rochford et al., Establishment of a cell line from embryos of the Cabbage Looper, *Trichoplusia ni* (Hubner), In Vitro 20: 823–825 (1984)) and (Granados et al., Replication of the *Trichoplusia ni* Granulosis and Nuclear Polyhedrosis Viruses in cell cultures, Virology 152: 472–476 (1986))), however, until fairly recently, a *Trichoplusia ni* embryonic cell line which is highly susceptible to numerous baculoviruses and efficiently supports replication of baculoviruses had not been established. Rochford et al. (1984) developed a *Trichoplusia ni* egg cell line (IPLB-TN-R) that is susceptible to only one of six baculoviruses tested, the *Autographa californica* multiply-enveloped nuclear polyhedrosis virus (AcMNPV). In addition, AcMNPV polyhedra production in the IPLB-TN-R cell line occurs later than desirable (beginning at 18 and 39 hours post infection), indicating an inefficient baculovirus replicating cell line. The BTI-TN-5B1-28 embryonic cell line reported by Granados et al. (1986) is moderately susceptible to infection by AcMNPV and *Trichoplusia ni* singly-enveloped nuclear polyhedrosis virus (TnSNPV).

U.S. Pat. Nos. 5,298,418, 5,300,435, 5,686,305, and 6,403,375 disclose several insect cell lines and the methods used for the establishment and development of novel insect cell lines; the complete disclosures of each of these patents are hereby incorporated herein by reference in their entirety.

BTI-TN-5B1-4 (sold by Invitrogen under the trade name "High 5" cells), as well as IPLB-SF 21 and its clone (Sf9), are the most widely used insect cell lines for the baculovirus expression vector system (Granados et al., J. Invertebr. Pathol., 1994, 64, 260–266; O'Reilly et al., 1992, Baculovirus expression vectors, A laboratory manual, W. H. Freeman and Company, NY). In most instances, High 5 cells provide superior production of recombinant proteins compared to Sf9 cells (Shuler et al., 1995, Baculovirus Expression Systems and Biopesticides, Wiley-Liss Inc., NY.). This high productivity is more evident in low passage culture of High 5 cells in comparison with high passage cells (Donaldson and Shuler, 1998, Biotechnol. Prog., 14, 543–547). This suggests that High 5 cells may be susceptible to detrimental effects associated with long term culturing.

SUMMARY OF THE INVENTION

Briefly stated, the invention provides new and useful cell lines from *Trichoplusia ni* (the cabbage looper), an insect species of the order Lepidoptera. The novel cell lines disclosed herein are derived from the well-known cell line BTI-TN-5B1-4 (ATC CRL 10859).

An embodiment of the invention provides two new isolated homogeneous cell lines, designated H5CL-B and H5CL-F (both of which are derived from the parental cell line BTI-TN-5B1-4, ATCC CRL 10859), wherein said novel cell lines possess the properties of increased production of baculovirus particles, increased expression of foreign proteins using a baculovirus expression system, and increased resistance to cell culture stress.

DETAILED DESCRIPTION OF THE INVENTION

Figure 1:
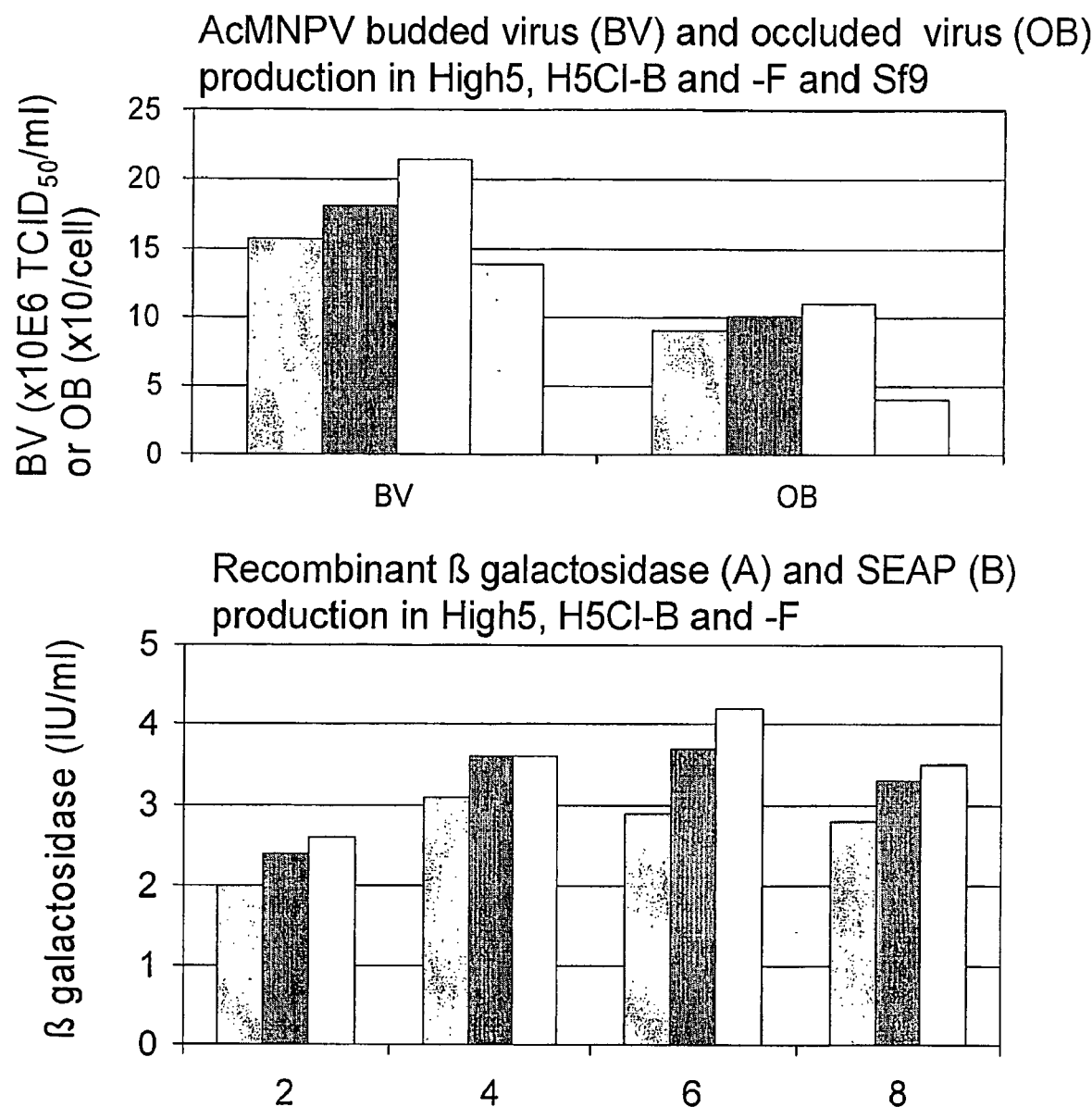
FIG. 1 provides graphical data depicting the improved features of the cell lines of the present invention. The top graph shows increased virus production in the cell lines; the bottom graph shows increased protein expression in the cell lines.
Figure 2:
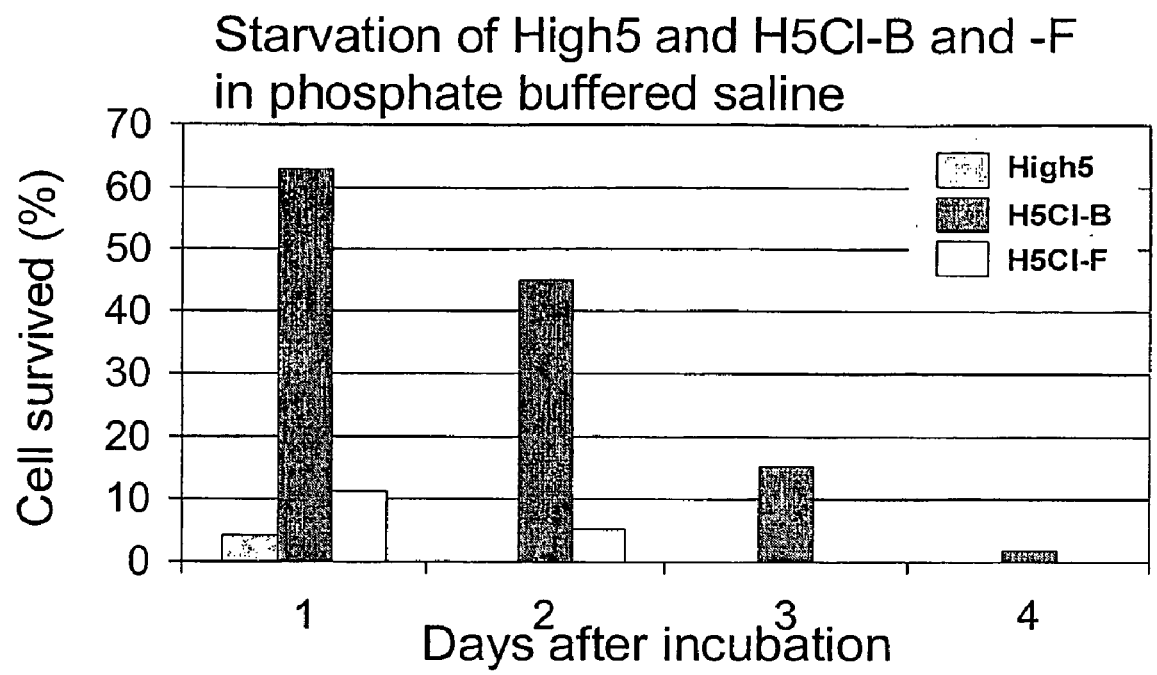
FIG. 2 provides graphical data depicting additional improved features of the cell lines of the present invention. The top graph shows increased survival (%) of the cell lines when subject to starvation. The bottom graph showing increased survival (%) of the cell lines when exposed to stress from Actinomycin-D at 24 hours post-treatment.
Figure 2:
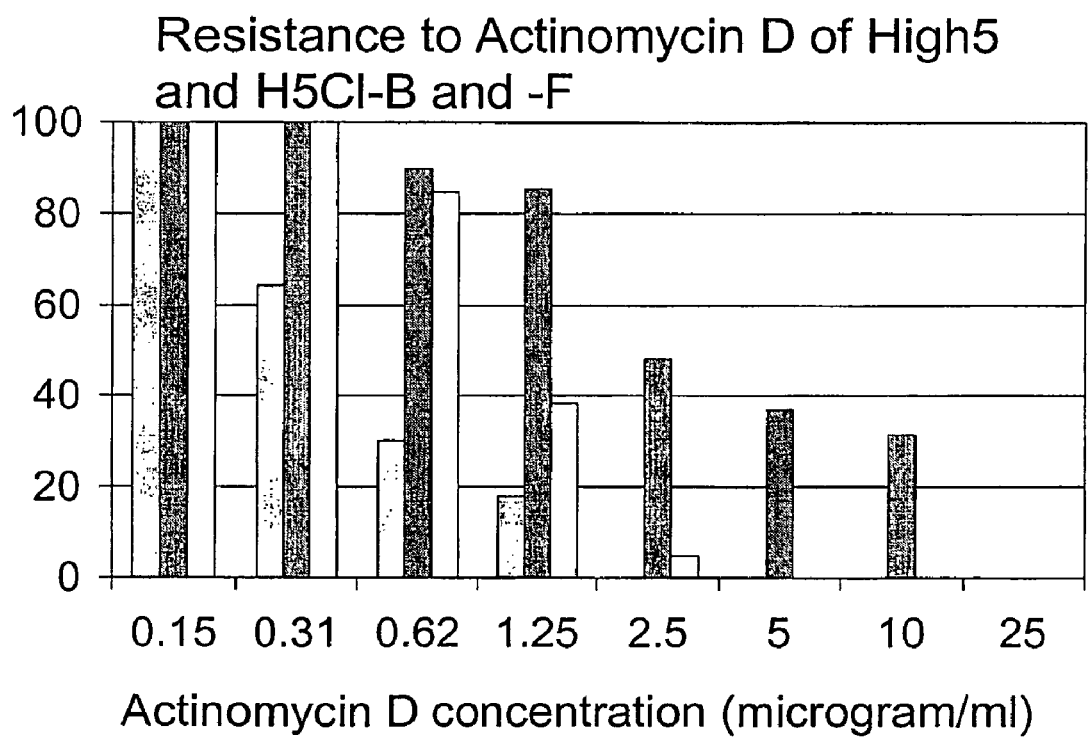
Figure 3:
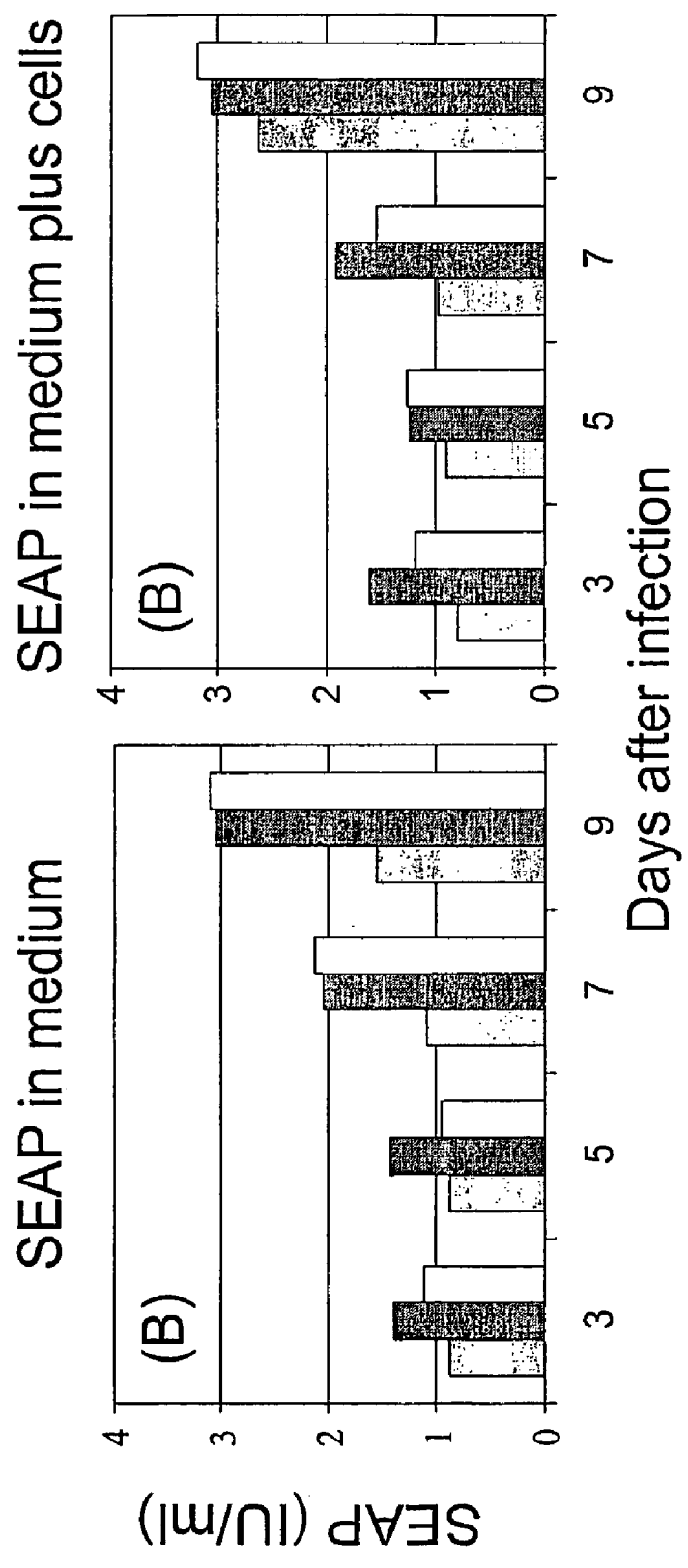
FIG. 3 provides graphical data showing increased expression of the SEAP protein in the novel cell lines of the invention, as harvested from the medium and from medium plus cells.

Abbreviations or definitions used in the disclosure are as follows: AcMNPV, *Autographa californica* multiply-enveloped nuclear polyhedrosis virus; TnSNPV, *Trichoplusia ni* singly-enveveloped nuclear polyhedrosis virus; MOI, multiplicity of infection; LDH, lactate dehydrogenase; MDH, malate dehydrogenase; NPV, nuclear polyhedrosis virus.

In this study we recloned the High 5 cells in order to preserve the high productivity characteristics of this cell line.

Establishment of BTI-TN-5B1-4 Line

A cell line was established from Lepidoptera, Noctuidae, *Trichoplusia ni*: BTI-TN-5B1-4, cloned from the low baculovirus susceptible *Trichoplusia ni* egg cell line BTI-TN-5B1-28.

A method for establishing a cell line from isolated tissue of insects is as follows: a) finely mincing said isolated insect tissue, with small dissecting scissors; b) shaking (e.g. 70 cycles/min) said isolated insect with a gentle proteolytic enzyme (e.g. dispase), 1% w/v, 5 units/ml in GTC-100 medium for 15 minutes at room temperature, to form dissociated cells and clumps of tissue; c) centrifuging said dissociated cells and said clumps of tissue at 50×g for 5 minutes; d) resuspending said dissociated cells in GTC-100 medium containing 100 @g/ml gentamicin sulfate (Sigma Chemical Co., St. Louis, Mo.) and 250 @g/ml Amphotericin B (Sigma Chemical Co.); e) seeding said cells into wells of a 24 multi-well disposable cell culture plate (Becton Dickinson and Co., Lincoln Park, N.J.); f) transferring said dissociated cells to disposable 25 cm$^2$ T flasks, when cells became crowded; g) changing said media every two weeks until the first subculture, approximately two months after the initiation of the cultures; h) maintaining said cell cultures at an appropriate temperature for growth, 28° C. in a modular incubator chamber (Vangard International, Neptune, N.J.); and I) flushing with an atmosphere high in oxygen, such as 95% oxygen/5% carbon dioxide, twice weekly.

The BTI-TN-5B1-4 cell line was cloned from a parental cell line (designated BTI-TN-5B1-28). The parental cell line was in the 28th passage and had been established from *Trichoplusia ni* eggs as described by Granados et al. (Virology 152, 472–476, 1986). The clone (BTI-TN-5B1-4) was obtained by diluting the parental cell line and seeding the suspended *Trichoplusia ni* cells into a 96 well microplate (0.1 ml cell suspension/well). The BTI-TN-5B1-4 clone arose from a single cell and, one week later, the cells were transferred into a 24 well microplate as the cell numbers increased. Within one month, the cells (BTI-TN-5B1-4) were transferred to a 25 cm$^2$ T flask for routine subculturing.

BTI-TN-5B1-4 cells were maintained in TNM-FH medium in Corning, T-25 cm$^2$ tissue culture flasks and were subcultured under aseptic conditions when a confluent monolayer is observed. Cell line BTI-TN-5B1-4 was switched from GTC-100 medium to the richer TNM-FH medium at passage 258. Cells were detached from flask walls by either a solid "wrist snap" of the flask or by using a rubber policeman. Initial seeding densities are between 2–3×10$^5$ cells/ml, which is represented by a split ratio of 0.3–0.5 ml cell suspension to 4.7–4.5 ml medium for 5B1-4 cells.

The BTI-TN-5B1-4 cell line has been accepted for deposit by the American Type Culture Collection (ATCC), 12301 Parklawn Drive, Rockville, Md. 20852, and will be made available under the terms and conditions imposed by the Budapest Treaty. The ATCC accession number of the BTI-TN-5B1-4 cell line is ATCC CRL 10859.

The new cell lines designated H5CL-B and H5CL-F have been deposited with the American Type Culture Collection (ATCC), 12301 Parklawn Drive, Rockville, Md. 20852, and will be made available under the terms and conditions imposed by the Budapest Treaty. The ATCC accession numbers of the new H5CL-B and H5CL-F cell lines PTA-5635 and PTA-5636, respectively.

Cell Growth Curves

Cells in log phase were subcultured into 25 cm$^2$ T flasks (Corning Glass Works, Corning, N.Y.). Cell densities were determined by counting the cell numbers within a microscope reticle of which the area at a certain objective was known. The cell densities in five areas of each flask were determined at 24 hour intervals. Cell population doubling time was calculated using the exponential formula described by Hayflick (Subculturing human diploid fibroblast cultures, Kruse and Patterson, Eds., New York: Academic Press 1973, pp. 220–223).

Test of Susceptibilities to Nuclear Polyhedrosis Viruses

Cells were cultured in 25 cm$^2$ T flasks and when the cell cultures were in the log growth phase, cell densities were determined by using a microscope reticle. The medium was aspirated and 1 ml of virus inocula was added to each flask (the inocula were prepared by diluting infectious media with TNM-FH medium so that all individual flasks were infected at a multiplicity of infection (MOI) of 5). The *Autographa californica* multiply-enveveloped nuclear polyhedrosis virus (AcMNPV) infectious medium used was 2nd passage produced in the IPLB-SF-21 AE cell line. The *Trichoplusia ni* singly-enveveloped nuclear polyhedrosis virus (TnSNPV) was a plaque purified isolate from which 1st passage infectious medium was produced in BTI-TN-5B1-4 cells. Polyhedra containing cells were counted at 4 days post inoculation (p.i.).

Isozyme Analysis

Cell samples were prepared and run on gels according to Corsaro and Fraser (Characterization of clonal populations of the *Heliothis zea* cell line IPLB-HZ 1075, In Vitro Cell. Dev. Bio. 23(12):855–862 (1987)). Briefly, monolayers of cells were harvested from 25 cm$^2$ T flasks. The cells were pelleted at 1800×g for 10 minutes, resuspended in 500 µl of cell grinding solution (0.15M Tris-Cl, pH 7.1, 46 mM citric acid, 10% sucrose, 1% Triton X-100, and 0.02 mM bromphenol blue), and lysed by crushing cells in a 0.5 ml micro tissue homogenizer. The lysate was cleared by centrifugation at 15,000×g for 3 minutes and the process was repeated to crush the cells for a second time. The cleared supernatants were stored in 30 µl aliquots at −70° C.

For sample separation, 0.75 mm vertical gels were used, 4.75%/0.25% acrylamide/bisacrylamide in 39 mM Tris HCl, pH 7.1, 8.5 mM sodium citrate (2×TC buffer). 10–20 µl of lysate were loaded onto each well, and the samples were separated at 350 V for 2 hours in TC buffer. The gels were stained for enzymes lactate dehydrogenase (LDH) and malate dehydrogenase (MDH) following the protocol of Harris and Hopkinson (Handbook of Enzyme Electrophoresis in Human Genetics, Amsterdam: North Holland Publishing Co. (1977), incorporated herein by reference, pages 68, 69).

Cell Line Growth Characteristics

Although oxygen supplementation was used to promote the initial establishment of the primary midgut cell line, once they were established on a regular subculturing schedule, non-oxygen supplemented sister flasks were derived from them. After a year of evaluation, it was concluded that the non-supplemented cells grew equally as well, and supplementation was discontinued.

The BTI-TN-5B1-4 insect cell line was derived from eggs of the cabbage looper, *Trichoplusia ni*. These cells have a diameter of approximately 20 μm and appear as a mixture of round and spindle shapes. The cytoplasm is also lightly granulated and the nucleus usually contain three to four nucleoli. The BTI-TN-5B1-4 cells attach firmly to flasks and form confluent layers after three to four days at 28° C.

Susceptibilities to Viruses

The BTI-TN-5B1-4 cell line was inoculated with baculoviruses AcMNPV and TnSNPV (both of which are members of the family Baculoviridae) at an MOI of 5 and then incubated. Polyhedra were present 14 to 16 hours post baculovirus infection. The percentages of polyhedra-containing (typical cytopathic effect of NPV infection) at 4 days p.i. are shown in Table 1. The number of polyhedra was determined by sonicating the infected cells, then centrifuging said cells, and finally counting the amount of polyhedra using a hemocytometer. The number of cells in each cell line was previously determined. The BTI-TN-5B1-4 cell line was highly susceptible to AcMNPV infection, with >95% of cells containing polyhedra. The BTI-TN-5B1-4 cell line also had high susceptibility to TnSNPV with 99% polyhedra-containing cells.

Establishment of Improved Clonal Cell Lines Designated H5CL-B and H5CL-F

The novel cell lines were obtained from the parental cell line using standard methods that are well known in the art. Briefly, low passage High 5 cells (High 5; passage 90) were adjusted for a cell density of 32 cells/ml, and dispensed as 1 ml cell suspension to each well of a cell cloning 24 well plate that consists of 16–2 mm square grid per well (Greiner Labotechnik). The grids that contained a single cell were marked, and the cultures were incubated at 28 degrees C. for one week. Thirty three cell colonies originated from single cells were transferred from the grids to individual wells of a 96 well plate, and subsequently to one of a 24 well plate. These clones were re-cloned two more times, using the same procedure. Finally, seven (7) cell clones were obtained and subjected to primary screening and selection, using techniques that are well known in the art. The parental High 5 cells, High 5 clone B (H5CL-B), and High 5 clone F (H5CL-F), were selected for further analysis. At the start of the comparative analysis, the High 5 cells and both clonal lines were at passage 161 and 43, respectively. The selected cell lines were then subjected to RAPD analysis, using a *T. ni* specific primer (5' ttgctgtcca 3').

*Autographa californica* MNPV (AcMNPV) Recombinant Virus Infection

β-galactosidase and secreted alkaline phosphatase (SEAP) expression from recombinant viruses were tested by standard published methods, which are well known in the art. All of the expression experiments were replicated 3 times.

Results

The results are shown in the Drawing. H5CL-B and H5CL-F have a unique shape, as shown in the Drawing. Further, the cells are resistant to Actinomycin D treatment and medium starvation in PBS, pH 7.0. Moreover, the novel cell lines H5CL-B and H5CL-F have increased recombinant protein production. More particularly, the two clonal lines, H5CL-B and H5CL-F possess superior productivity of AcMNPV and recombinant β-galactosidase and SEAP. The new clones outperform the High 5 cells to the following extent: at 6 days after infection with a r-baculovirus with the B-gal gene, clones B and F produce 1.3× and 1.5× more Beta Gal, respectively, than the High 5 cells. At 9 days after infection with the virus carrying the SEAP gene, clones B and F produce 2× more secreted SEAP than the High 5 cells. It is important to note that both clones (especially clone B) are much more resistant to culture insult (PBS or Actinomycin D) than the High 5 cells.

It should be noted that the BV production data for the different cell lines listed in FIG. 4 are incorrect in the Drawing. The correct data for the yield of BV for the different lines are: Clone B, $3.29 \times 10^7$; Clone F, $3.62 \times 10^7$, High 5 cells, $2.94 \times 10^7$, and SF9 cells, $1.53 \times 10^8$ TCID50/ml.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A cloned cell line identified as H5CL-B (ATCC Accession number PTA-5635), derived from parental cell line BT1-TN-5B1-4, wherein said cloned cell line possesses the properties of increased production of baculovirus particles, increased expression of foreign proteins using a baculovirus expression system, and increased resistance to cell culture stress, relative to said parental cell line.

2. A cloned cell line identified as H5CL-F (ATCC Accession number PTA-5636), derived from parental cell line BT1-TN-5B1-4, wherein said cloned cell line possesses the properties of increased production of baculovirus particles, increased expression of foreign proteins using a baculovirus expression system, and increased resistance to cell culture stress, relative to said parental cell line.

* * * * *